United States Patent

Yanagi et al.

[11] Patent Number: 5,502,204
[45] Date of Patent: Mar. 26, 1996

[54] PROCESS FOR THE PREPARATION OF 1-SUBSTITUTED-5(4H)-TETRAZOLINONES

[75] Inventors: Akihiko Yanagi, Tochigi; Yukiyoshi Watanabe, Saitama; Shin-ichi Narabu, Ibaraki, all of Japan

[73] Assignee: Nihon Bayer Agrochem K.K., Tokyo, Japan

[21] Appl. No.: 301,509

[22] Filed: Sep. 7, 1994

[30] Foreign Application Priority Data

Sep. 14, 1993 [JP] Japan .................................. 5-250907

[51] Int. Cl.⁶ .................. C07D 257/02; C07D 403/04; C07D 413/04; C07D 417/04
[52] U.S. Cl. .................. 548/251; 544/105; 546/276; 548/136; 548/178; 548/217
[58] Field of Search ............................... 548/251

[56] References Cited

U.S. PATENT DOCUMENTS

| | | | |
|---|---|---|---|
| 2,386,869 | 10/1945 | Kendall | 260/308 |
| 4,956,469 | 9/1990 | Covey et al. | 548/251 |
| 5,003,075 | 3/1991 | Covey et al. | 548/251 |
| 5,019,152 | 5/1991 | Covey et al. | 548/251 |

FOREIGN PATENT DOCUMENTS

| | | |
|---|---|---|
| 146279 | 6/1985 | European Pat. Off. . |
| 202929 | 11/1986 | European Pat. Off. . |

OTHER PUBLICATIONS

J. Org. Chem 33 (1) 262–265 (1968).

*Primary Examiner*—David B. Springer
*Attorney, Agent, or Firm*—William C. Gerstenzang; Sprung Horn Kramer & Woods

[57] ABSTRACT

A process for the preparation of a 1-substituted-5(4H)-tetrazolinone of the formula

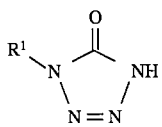

(I)

wherein
$R_1$ is defined in the specification
n is 0, 1, 2, 3 or 4, which comprises reacting a 1-substituted-5(4H)-tetrazolinethione of the formula

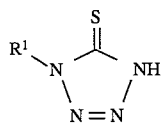

(II)

with an ethylene oxide of the formula

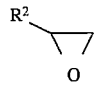

(III)

wherein
$R^2$ represents hydrogen, methyl or ethyl,
in the presence of a base and in the presence of water, an alcohol or a mixture thereof.

4 Claims, No Drawings

PROCESS FOR THE PREPARATION OF 1-SUBSTITUTED-5(4H)-TETRAZOLINONES

The present invention relates to a process for the preparation of 1-substituted-5(4H)-tetrazolinones.

In general, 1-substituted-5(4H)-tetrazolinones can be synthesized by known processes according to the following reaction schemes:

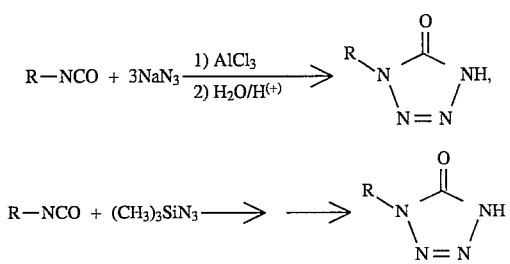

These reactions have been found not to be useful industrially because:

1) the reactions are of non-aqueous nature and the reaction procedures and suitable reaction conditions are difficult to select,
2) isocyanates starting materials, particularly methylisocyanate and heterocyclic isocyanates, are difficult to manufacture and handle,
3) in reactions using aluminum chloride, only 1 mol of the expensive sodium azide reacts per mol of isocyanate with the remaining two mols of unreacted sodium azide being decomposed and discarded,
4) aluminum chloride to be used as catalyst in the reaction is difficult to dispose of by drainage, and
5) azidotrimethylsilane is more expensive than sodium azide, and the yield of product is sometimes low even with a prolonged reaction time.

Further, the Journal of Organic Chemistry, 33 (I), 262–265 (1968) discloses the following reaction with a yield of 45%:

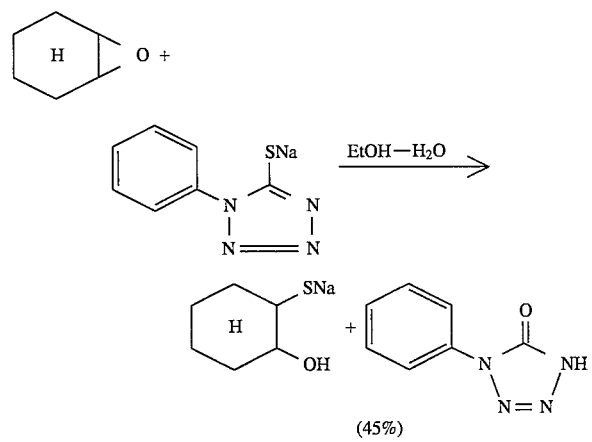

It has now been found that 1-substituted-5(4H)-tetrazolinones of the general formula (I)

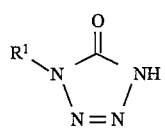

wherein
$R^1$ represents optionally substituted $C_{1-12}$ alkyl, optionally substituted $C_{3-8}$ cycloalkyl, optionally substituted $C_{3-8}$ alkenyl, optionally substituted $C_{3-8}$ alkynyl, or a group of the general formula

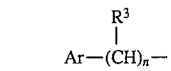

wherein
Ar represents optionally substituted phenyl, optionally substituted naphthyl or an optionally substituted five- to seven-membered heterocyclic ring,
$R^3$ represents hydrogen or $C_{1-4}$ alkyl, and
n is 0, 1, 2, 3 or 4,
are obtained when 1-substituted-5(4H)-tetrazolinethiones of the general formula (II)

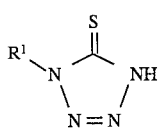

are reacted with ethylene oxides of the general formula (III)

wherein
$R^2$ represents hydrogen, methyl or ethyl,
in the presence of a base and in the presence of water or an alcohol or a mixture thereof.

Surprisingly, it has been found that the process according to the present invention has the following advantages as compared with the above-mentioned prior art processes wherein isocyanates are reacted with sodium azide:

1) an excellent yield is realized,
2) 1-substituted-5(4H)-tetrazolinethiones of the general formula (II) employed as starting materials according to the present invention are less expensive than the starting materials previously used for the production of 1-substituted-5(4H)-tetrazolinones, yet capable of producing a variety of compounds,
3) the reaction solvents employed are not expensive, and
4) the reaction can readily be carried out on an industrial scale.

In the present invention, if use is made, as starting materials, of 1-phenyl-5(4H)-tetrazolinethione and propylene oxide, for example, the reaction can be expressed as follows:

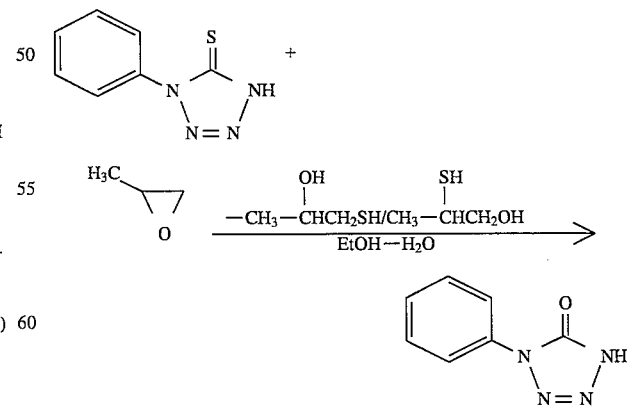

In the general formula (II), representing 1-substituted-5(4H)-tetrazolinethiones, starting compounds of the present invention, $R^1$ may be any substituent excluding very reactive ones, such as a mercapto group, primary amino, etc., so that the process of the present invention can be widely employed in the production of 1-substituted 5(4H)-tetrazolinones.

In the general formula (II), $R^1$ preferably represents $C_{1-12}$ alkyl, $C_{1-6}$ haloalkyl, $C_{2-8}$ alkoxyalkyl, $C_{2-8}$ alkylthioalkyl, $C_{3-8}$ cycloalkyl, $C_{3-8}$ alkenyl, $C_{3-8}$ haloalkenyl, $C_{3-8}$ alkynyl, or a group of the general formula

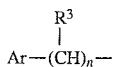

wherein

Ar represents unsubstituted phenyl, or a phenyl group having a substituent or substituents optionally selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, —$NR^4R^5$, $C_{1-4}$-alkoxy-carbonyl, carboxy, optionally substituted phenoxy, optionally substituted heterocyclyl-oxy, methylene dioxy, halomethylene dioxy, ethylene dioxy, haloethylene dioxy, cyano and nitro;
or Ar represents unsubstituted naphthyl, or a substituted naphthyl group having a substituent or substituents optionally selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, —$NR^4R^5$, $C_{1-4}$ alkoxy-carbonyl, carboxy, optionally substituted phenoxy, optionally substituted heterocyclyl-oxy, methylene dioxy, halomethylene dioxy, ethylene dioxy, haloethylene dioxy, cyano and nitro;
or Ar represents a five- to seven-membered heterocyclic ring or its benzologues or their substituted derivatives having a substituent or substituents optionally selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, —$NR^4R^5$, $C_{1-4}$ alkoxy-carbonyl, carboxy, optionally substituted phenoxy, optionally substituted heterocyclyl-oxy, methylene dioxy, halomethylene dioxy, ethylene dioxy, haloethylene dioxy, cyano and nitro, $R^3$ represents hydrogen or $C_{1-4}$ alkyl, $R^4$ and $R^5$ may be the same or different and represent hydrogen or $C_{1-4}$ alkyl, and n represents 0, 1, 2 or 3.

More preferably, $R^1$ represents methyl, ethyl, n-propyl, isopropyl, n-(sec-, iso-, or tert-)butyl, n-hexyl, trifluoromethyl, difluoromethyl, chlorodifluoromethyl, 2,2,2-trifluoroethyl, perfluoropropyl, perfluorohexyl, methoxyethyl, ethoxymethyl, ethoxyethyl, propoxyethyl, butoxyethyl, methylthioethyl, methylthiomethyl, methylthiopropyl, ethylthiomethyl, ethylthioethyl, propylthioethyl, butylthioethyl, cyclopropyl, cyclobutyl, cyclopentyl, cyclohexyl, allyl, chloroallyl, butenyl, hexenyl, propargyl, or a group of the general formula

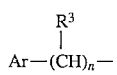

wherein

Ar represents unsubstituted phenyl or a phenyl group having a substituent or substituents optionally selected from the group consisting of fluorine, chlorine, bromine, methyl, ethyl, propyl, butyl, difluoromethyl, chlorodifluoromethyl, trifluoromethyl, 2,2,2-trifluoroethyl, methoxy, ethoxy, propoxy, butoxy, difluoromethoxy, chlorodifluoromethoxy, trifluoromethoxy, 2,2,2-trifluoroethoxy, methylthio, ethylthio, propylthio, difluoromethylthio, trifluoromethylthio, 2,2,2-trifluoromethylthio, dimethylamino, diethylamino, methoxycarbonyl, ethoxycarbonyl, butoxycarbonyl, carboxy, optionally substituted phenoxy, optionally substituted heterocyclyl-oxy, (wherein the hetero ring of said heterocyclyl-oxy is selected from the group consisting of imidazole, pyrazole, triazole, oxazole, isoxazole, benzoxazole, thiazole, isothiazole, benzothiazole, oxadiazole, thiadiazole, tetrazole, pyridine, quinoline, isoquinoline, pyrimidine, pyridazine, pyrazine, quinazoline, quinoxaline, triazine, thiophene, benzothiophene, furan and benzofuran), methylenedioxy, difluoromethylenedioxy, ethylenedioxy, chlorodifluoroethylenedioxy, difluoroethylenedioxy, trifluoroethylenedioxy, tetrafluoroethylenedioxy, cyano and nitro;
or Ar represents unsubstituted naphthyl or a substituted naphthyl group having a substituent or substituents optionally selected from the group consisting of fluorine, chlorine, bromine, methyl, ethyl, propyl, butyl, difluoromethyl, chlorodifluoromethyl, trifluoromethyl, 2,2,2-trifluoroethyl, methoxy, ethoxy, propoxy, butoxy, difluoromethoxy, chlorodifluoromethoxy, trifluoromethoxy, 2,2,2-trifluoroethoxy, methylthio, ethylthio, propylthio, difluoromethylthio, trifluoromethylthio, 2,2,2-trifluoroethylthio, dimethylamino, diethylamino, methoxycarbonyl, ethoxycarbonyl, butoxycarbonyl, carboxy, optionally substituted phenoxy, optionally substituted heterocyclyl-oxy, (wherein the hereto ring of said heterocyclyl-oxy is selected from the group consisting of imidazole, pyrazole, triazole, oxazole, isoxazole, benzoxazole, thiazole, isothiazole, benzothiazole, oxadiazole, thiadiazole, tetrazole, pyridine, quinoline, isoquinoline, pyrimidine, pyridazine, pyrazine, quinazoline, quinoxaline, triazine, thiophene, benzothiophene, furan and benzofuran), methylenedioxy, difluoromethylenedioxy, ethylenedioxy, chlorodifluoroethylenedioxy, difluoroethylenedioxy, trifluoroethylenedioxy, tetrafluoroethylenedioxy, cyano and nitro;
or Ar represents an unsubstituted five- to six-membered heterocyclic ring or its benzologues, (wherein said hetero ring is selected from the group consisting of imidazole, pyrazole, triazole, oxazole, isoxazole, benzoxazole, thiazole, isothiazole, benzothiazole, oxadiazole, thiadiazole, tetrazole, pyridine, quinoline, isoquinoline, pyrimidine, pyridazine, pyrazine, quinazoline, quinoxaline, triazine, thiophene, and furan), a five- or six-membered heterocyclic ring or their benzologues (wherein said heterocyclic ring is selected from the group consisting of imidazole, pyrazole, triazole, oxazole, isoxazole, benzoxazole, thiazole, isothiazole, benzthiazole, oxadiazole, thiazole, tetrazole, pyridine, quinoline, isoquinoline, pyrimidine, pyridazine, pyrazine, quinazoline, quinoxaline, triazine, thiophene and furan), having a substituent or substituents optionally selected from the group consisting of fluorine, chlorine, bromine, methyl, ethyl, propyl, butyl, difluoromethyl, chlorodifluoromethyl, trifluoromethyl, 2,2,2-trifluoroethyl, methoxy, ethoxy, propoxy, butoxy, difluoromethoxy, chlorodifluoromethoxy, trifluoromethoxy, 2,2,2-trifluoroethoxy, methylthio, ethylthio, propylthio, difluoromethylthio, trifluoromethylthio, 2,2,2-trifluoromethylthio, dimethylamino, diethylamino, methoxycarbonyl, ethoxycarbonyl, butoxycarbonyl, carboxy, optionally substituted phenoxy, optionally substituted heterocyclyl-oxy, (wherein the hetero ring of said heterocyclyl-oxy is selected from the group consisting of imidazole, pyrazole, triazole, oxazole, isoxazole, benzoxazole, thiazole, isothiazole, benzothiazole, oxadiazole, thiadiazole, tetrazole, pyridine, quinoline, isoquinoline, pyrimidine, pyridazine, pyrazine, quinazoline, quinoxaline, triazine, thiophene, benzothiophene, furan and benzofuran), methylene dioxy, difluoromethylene dioxy, ethylene dioxy, chlorodifluoroethylene dioxy, difluoroethylene dioxy, trifluoroethylene dioxy, tetrafluoroethylene dioxy, cyano and nitro, $R^3$ represents hydrogen or methyl and n represents 0, 1 or 2.

The 1-substituted-5(4H)-tetrazolinethiones of the formula (II) can be synthesized for example, by reacting a compound of the general formula (IV)

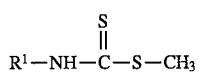
(IV)

with one equivalent of sodium azide in water.

This reaction is disclosed in U.S. Pat. No. 2,386,869 and Japanese Laid-open No. Sho 53-50, 169. The compounds of formula (IV), used as starting materials in this reaction, are well known in the field of organic chemistry.

For an alternative route to 1-aryl-5(4H)-tetrazolinethiones of the formula (II), namely by reacting 4-aryl-thiosemicarbazides with nitrous acid ($HNO_2$), see "Berichte", Vol. 28, pp. 74–76 (1895).

The ethylene oxides represented by the general formula (III) are also well known in organic chemistry.

As ethylene oxides of the general formula (III) there may be mentioned ethylene oxide, propylene oxide and 1,2-epoxybutane and, as most preferred examples, ethylene oxide and propylene oxide.

In carrying out the process according to the present invention use is made of suitable diluents. Examples of such diluents are water and alcohols such as, for example, methanol, ethanol, isopropanol, butanol and mixtures thereof.

The process of the present invention is carried out in the presence of bases which include hydroxides, carbonates and bicarbonates of alkali metals or alkaline earth metals such as, for example, sodium bicarbonate, potassium bicarbonate, sodium carbonate, potassium carbonate, lithium hydroxide, sodium hydroxide, potassium hydroxide and calcium hydroxide.

The process according to the present invention can be conducted over a substantially wide range of temperature. In general, the reaction is carried out at temperatures in the range of from about −30° C. to about +50° C., preferably about 0° C. to about +30° C. The reaction is preferably carried out at normal pressure but it may be carried out at elevated or reduced pressure as well.

The reaction time may range from one hour to twelve hours, preferably from one hour to six hours.

In carrying out the present process, from 1.0 mol to 1.3 mols of ethylene oxides of the general formula (III) are reacted with 1 mol of 1-substituted-5(4H)-tetrazolinethione of the general formula (II) in the presence of a diluent such as, for example, a solvent mixture consisting of water and ethanol and from 1 mol to 1.2 mols of a base, so as to obtain the aimed compounds.

1-Substituted-5(4H)-tetrazolinones are useful as starting materials for the production of herbicidal compounds as disclosed by U.S. Pat. Nos. 4,956,469, 5,003,075 and 5,019, 152; EP-A- 146,279 and EP-A-202,929.

The process according to the present invention will be further described in the following illustrative examples:

EXAMPLES:

Synthesis Example 1

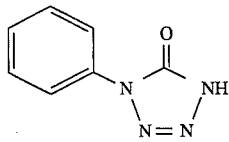

Sodium hydroxide (0.84 g) was dissolved in water (1 ml), followed by addition of 1-phenyl- 5(4H)-tetrazolinethione (3.56 g) thereto so as to form a uniform solution. The thus obtained solution was diluted with ethanol (25 ml) and then cooled to 0° C., followed by dropwise addition of propylene oxide (1.51 g) thereto with the temperature being kept at 0° C. After a 30 minute-stirring at 0° C, the reaction was continued for five hours at room temperature. The solvent was then removed from the reaction product by reduced pressure distillation, followed by addition of water (30 ml) to the residue from which instable oil was washed away with ethyl acetate. The resulting aqueous layer was withdrawn and acidified with dilute hydrochloric acid, followed by filtration of the separated crystals. After washing of the thus obtained crystals with cold water and then drying, there was obtained 1-phenyl-5(4H)-tetrazolinone (2.33 g) having a melting point (m.p.) in the range of 191° to 192° C.

Synthesis Example 2

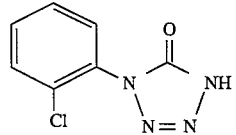

Sodium hydroxide (0.52 g) was dissolved in water (1 ml), followed by addition of 1-( 2-chlorophenyl)-5(4H)-tetrazolinethione (2.13 g) thereto so as to form a uniform solution. The thus obtained solution was diluted with ethanol (25 ml) and then cooled to 0° C., followed by dropwise addition of propylene oxide (0.76 g) thereto with the temperature being kept at 0° C. After a 30 minute-stirring at 0° C., the reaction was continued for five hours at room temperature. The solvent was then removed from the reaction product by reduced pressure distillation, followed by addition of water (30 ml) to the residue from which insoluble oil was washed away with ethyl acetate. The resulting aqueous layer was withdrawn and acidified with hydrochloric acid, followed by extraction of the separated crystals with ethyl acetate and drying of the ethyl acetate solution over anhydrous magnesium sulfate. Upon removal of the solvent by reduced pressure distillation there was obtained 1-(2-chlorophenyl)-5(4H)-tetrazolinone (1.92 g) having a m.p. in the range of 124° to 126° C.

Synthesis Example 3

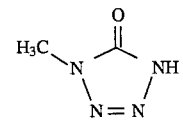

1-Methyl-5(4H)-tetrazolinethione (5.81 g), sodium hydroxide (2.60 g) and propylene oxide (3.78 g), were reacted in a manner similar to that employed in Synthesis Examples 1 and 2. The resulting aqueous layer was acidified and then evaporated to dryness at reduced pressure followed by the resulting residue being extracted into ethyl acetate and filtration. Upon removal of the solvent by reduced pressure distillation there was obtained 1-methyl-5(4H)-tetrazolinone (3.66 g) having a m.p. in the range of 114° to 116.5° C.

sodium hydroxyide (1.7 g) and cyclohexene oxide (4.1 g) to obtain 1-phenyl-5(4H)-tetrazolinone (3.1 g, in a yield of 48%). On working up, the reaction produced material insoluble in alkali, thus resulting in difficulty in the purification of the desired product.

In the following Table 1 there are shown further compounds of the above formula (I) that were synthesized in a manner analogous to that described in each of the foregoing Synthesis Examples 1–3, together with three compounds obtained according to such foregoing examples.

TABLE 1

| Ex. No. | $R^1$ | $R^2$ | Base | Solvent | Yield (%) | Physical constant of product (I) |
|---|---|---|---|---|---|---|
| 1 | Phenyl | Methyl | Sodium-hydroxide | Ethanol | 95 | m.p. 191–192° C. |
| 1a | Phenyl | Methyl | Potassium-hydroxide | Ethanol | 82 | m.p. 191–192° C. |
| 1b | Phenyl | Methyl | Sodium-hydroxide | Water | 88 | m.p. 191–192° C. |
| 1c | Phenyl | Ethyl | Sodium-hydroxide | Ethanol | 85 | m.p. 191–192° C. |
| 2 | 2-chlorophenyl | Methyl | Sodium-hydroxide | Ethanol | 97 | m.p. 124–126° C. |
| 2a | 2-chlorophenyl | Hydrogen | Sodium-hydroxide | Ethanol | 80 | m.p. 124–126° C. |
| 3 | Methyl | Methyl | Sodium-hydroxide | Ethanol | 83 | m.p. 114–116.5° C. |
| 4 | 2-chloro-3-methylphenyl | Methyl | Sodium-hydroxide | Ethanol | 81 | m.p. 121–123.5° C. |
| 5 | 3,5-dichlorophenyl | Methyl | Sodium-hydroxide | Ethanol | 91 | m.p. 198–189.5° C. |
| 6 | 2-chloro-4-trifluoromethyl-phenyl | Methyl | Sodium-hydroxide | Ethanol | 87 | m.p. 155.5–157° C. |
| 7 | Benzyl | Methyl | Sodium-hydroxide | Ethanol | 84 | m.p. 145.5–147° C. |
| 8 | 3,4-tetrafluoro-ethylenedioxy-phenyl | Methyl | Sodium-hydroxide | Ethanol | 86 | m.p. 123–123.5° C. |
| 9 | 2-chloro-5-pyridyl-methyl | Methyl | Sodium-hydroxide | Ethanol | 82 | m.p. 141–142.5° C. |

Comparative Synthesis Example

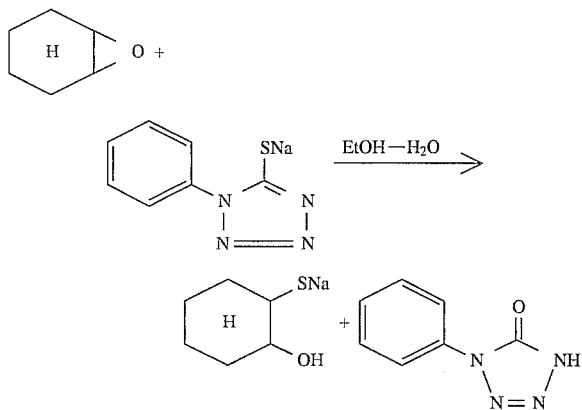

According to a description given in "Journal of Organic Chemistry", 33 (1), 262–265 (196B), use was made, for reaction, of 1-phenyl-5(4H)-tetrazolinethione (7.1 g), In addition to the above-mentioned compounds, the foilcrying compounds can also be obtained in high yields according to the reaction conditions mentioned above:

1-(ethyl)-5(4H)-tetrazolinone, 1-(n-propyl)-5(4H)-tetrazolinone, 1-(isopropyl)-5(4H)-tetrazolinone, 1-(tert-butyl)-5(4H)-tetrazolinone, 1-(cyclopropyl)-5(4H)-tetrazolinone, 1-(cyclopentyl)-5(4H)-tetrazolinone, 1-(cyclohexyl)-5(4H)-tetrazolinone, 1-(2,2,2-trifluoroethyl)-5(4H)-tetrazolinone, 1-(methoxyethyl)-5(4H)-tetrazolinone, 1-(ethylthioethyl)-5(4H)-tetrazolinone, 1-(methylthioethyl)-5(4H)-tetrazolinone, 1-(allyl)-5(4H)-tetrazolinone, 1-(3-chloroallyl)-5(4H)-tetrazolinone, 1-(propargyl)-5(4H)-tetrazolinone, 1-(2-fluorophenyl)-5(4H)-tetrazolinone, 1-(3-chlorophenyl)-5(4H)-tetrazolinone, 1-(3-trifluoromethylphenyl)-5(4H)-tetrazolinone, 1-(4-trifluoromethylphenyl)-5(4H)-tetrazolinone, 1-(4-chlorophenyl)-5(4H)-tetrazolinone, 1-(2-methylphenyl)-5(4H)-tetrazolinone, 1-(3-methylphenyl)-5(4H)-tetrazolinone, 1-(4-methylphenyl)-5(4H)-tetrazolinone, 1-(2-methoxyphenyl)-5(4H)-tetrazolinone, 1-(4-methoxyphenyl)-5(4H)-tetrazolinone, 1-(4-trifluoromethoxyphenyl)-5(4H)-tetrazolinone, 1-(4-trifluoromethylphenyl)-5(4H)-tetrazolinone, 1-(3-propylphenyl)-5(4H)-tetrazolinone, 1-(4-tert-butylphenyl)-5(4H)-tetrazolinone, 1-(2,4-dichlorophenyl)-5(4H)-tetrazolinone, 1-(2,6-dichlorophenyl)-5(4H)-tetrazolinone, 1-(2-chloro-6-methylphenyl)-5(4H)-tetrazolinone, 1-(3-chloro-4-trifluoromethylphenyl)-5(4H)-tetrazolinone, 1-[4-(2,4-dichlorophenoxy)phenyl]-5(4H)-tetrazolinone, 1-[4-(2-chloro-4-trifluoromethylphenoxy)phenyl]-5(4H)-tetrazolinone, 1-[4-(2,6-dichloro-4-trifluoromethylphenoxy)-phenyl]-5(4H)-tetrazolinone, 1-(3-phenoxyphenyl)-5(4H)-tetrazolinone, 1-(3,4-difluoromethylenedioxyphenyl)-5(4H)-tetrazolinone, 1-[4-(3,5-dichloropyridinyloxy)-phenyl]-5(4H)-tetrazolinone, 1-[3,5-bis(trifluoromethyl)-phenyl]-5(4H)-tetrazolinone, 1-(2-cyanophenyl)-5(4H)-tetrazolinone, 1-(4-chloro-2-fluoro-5-isopropoxyphenyl)-5(4H)-tetrazolinone, 1-[4-chloro-2-fluoro-5-(methoxycarbonyl)methoxyphenyl]- 5(4H)-tetrazolinone, 1-[4-chloro-2-fluoro-5-(n-pentyloxycarbonyl)methoxyphenyl]-5-(4H)-tetrazolinone, 1-[7-fluoro-4-ethoxy-2H-1,4-benzoxazine-3(4H)-one-6-yl]-5(4 H)-tetrazolinone, 1-[7-fluoro-4-propargyl-2H-1,4-benzoxazine-3(4H)-one-6-yl]-5(4 H)-tetrazolinone 1-(6-fluoro-4-propargyl-2H-1,3-benzoxazole-2-one-5-yl)-5(4H)-tetrazolinone, 1-(6-fluoro-4-propargyl-2H-1,3-benzothiazole-2-one-5-yl)-5(4H)-tetrazolinone, 1-[4-chloro-2-fluoro-5-(methanesulphonylamino)-phenyl]-5(4H)-tetrazolinone, 1-(3-tert-butylisoxazole-5-yl)-5(4H)-tetrazolinone, 1-(5-tert-butylisoxazole-5-yl)-5(4H)-tetrazolinone, 1-(5-tert-butyl- 1,3,4-thiadiazol-2-yl)-5(4H)-tetrazolinone, 1-(5-trifluoromethylpyridine-2-yl)-5(4H)-tetrazolinone, and 1-(3-chloro-5-trifluoromethyl-pyridine-2-yl)-5(4H)-tetrazolinone.

It is understood that the specification and examples are illustrative but not limitative of the present invention and that other embodiments within the spirit and scope of the invention will suggest themselves to those skilled in the art.

We claim:

1. A process for the preparation of a 1-substituted-5(4H)-tetrazolinone of the formula

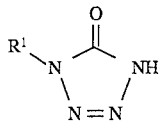

(I)

wherein

R¹ represents 7-fluoro-4-ethoxy-2H-1,4-benzoxazine 3(4H)-one- 5(4H)-yl, which comprises reacting a 1-substituted-5(4H)-tetrazolinethione of the formula

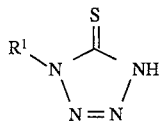

(II)

with an ethylene oxide of the formula

(III)

wherein

R² represents methyl, and said 1-substituted-5(4H)-tetrazoline is 1-[7-fluoro-4-ethoxy-2H-1,4-benzoxazine-3(4H)-one-6-yl]-5-(4H)-one-6-yl] -5(4H) -tetrazolinone in the presence of a base and in the presence of water, an alcohol or a mixture thereof at a temperature of from −30° C. to +50° C., for a time of 1 to 12 hours and wherein the compound of formula (III) is present in an amount of from 1.0 to 1.3 mols per tool of the compound of formula (II), and the base is present in an amount of 1.0 to 1.2 mols per mol of the compound of formula (II), said base being a member of the group consisting of the hydroxides, carbonates and bicarbonates of alkali metals or alkaline earth metals.

2. The process of claim 1 wherein R¹ is 7-fluoro-4-propargyl- 2H-1,4-benzoxazine 3(4H)-one-5(4H)-yl, R² is methyl and said 1-substituted-5(4H)-tetrazoline is 1-[7-fluoro-4-progaryl- 2H-1,4-benzoxazine-3(4H)-one-6-yl]-5(4H)-tetrazolinone.

3. A process for the preparation of a 1-substituted- 5(4H)-tetrazolinone of the formula

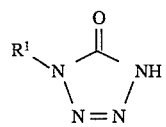

(I)

wherein

R¹ represents 7-fluoro-4-propargyl-2H-1,4-benzoxazine 3(4H)-one- 5(4H)-yl, which comprises reacting a 1-substituted-5(4H)-tetrazolinethione of the formula

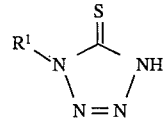

(II)

with an ethylene oxide of the formula

(III)

wherein

R² represents methyl, and said 1-substituted-5(4H) -tetrazoline is 1- [7-fluoro-4-progaryl- 2H-1,4-benzoxazine-3(4H)-one-6-yl]-5(4H)-tetrazolinone in the presence of a base and in the presence of water, an alcohol or a mixture thereof at a temperature of −30° C. to +50° C., for a time of 1 to 12 hours and wherein the compound of formula (III) is present in an amount of from 1.0 to 1.3 mols per mol of the compound of formula (II), and the base is present in an amount of 1.0 to 1.2 mols per mol of the compound of formula (II), said base being a member of the group consisting of the hydroxides, carbonates and bicarbonates of alkali metals or alkaline earth metals.

4. A process for the preparation of a 1-substituted-(4H)-tetrazolinone of the formula

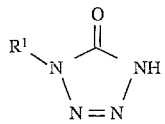 (I)

wherein $R^1$ represents $C_{1-12}$ alkyl, $C_{3-8}$ cycloalkyl, $C_{3-8}$ alkenyl, $C_{3-8}$ alkynyl, each of which may be substituted by one or more of F, Cl, $C_{1-4}$ alkoxy or a group of the formula

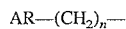

wherein

Ar represents unsubstituted phenyl or a phenyl group having a substituent or substituents selected from the group consisting fluorine, chlorine, cyano, $C_{1-4}$ alkyl, trifluoromethyl, $C_{1-4}$ alkoxy, trifluoromethoxy, methansulfonylamino, methoxycarbonyl, $C_{1-6}$ alkoxycarbonylmethoxy, phenoxy which may be substituted by Cl or $CF_3$, pyridyloxy, difluoroethylenedioxy, tetrafluoroethylenedioxy, or Ar represents pyridyl, 1,4-benzoxazine-3(4H)-one-6-yl, 1,3-benzoxazole-2-one-5-yl, 1,3-benzothiazole-2-one-5-yl, isoxazolyl, or 1,3,4-thiadiazolyl optionally substituted by a substituent selected from the group consisting of fluorine, chlorine. $C_{1-4}$ alkyl, trifluoromethyl, $C_{1-4}$ alkoxy, and n is 0 or 1, which comprises reacting a 1-substituted-5(4H)-tetrazolinethione of the formula

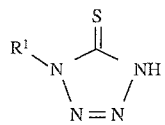

with an ethylene oxide of the formula

wherein $R^2$ represents hydrogen, methyl or ethyl.

* * * * *

UNITED STATES PATENT AND TRADEMARK OFFICE
CERTIFICATE OF CORRECTION

PATENT NO. : 5,502,204
DATED : March 26, 1996
INVENTOR(S) : Yanagi, et al.

It is certified that error appears in the above-indentified patent and that said Letters Patent is hereby corrected as shown below:

Col. 10, line 31    Delete " tool " and substitute -- mol --

Col. 11, line 12    After " substituted- " insert -- 5 --

Signed and Sealed this

Twentieth Day of August, 1996

*Attest:*

BRUCE LEHMAN

*Attesting Officer*    *Commissioner of Patents and Trademarks*